United States Patent [19]

Kühn

[11] Patent Number: 5,676,134
[45] Date of Patent: Oct. 14, 1997

[54] RESPIRATORY GAS CONTAINER

[75] Inventor: Hans-Joachim Kühn, Wiesbaden, Germany

[73] Assignee: Heraeus Med GmbH, Hanau, Germany

[21] Appl. No.: 554,333

[22] Filed: Nov. 6, 1995

[30] Foreign Application Priority Data

Nov. 8, 1994 [DE] Germany ............ 44 39 474.8

[51] Int. Cl.$^6$ ................................ A61M 16/00
[52] U.S. Cl. ...................... 128/205.13; 128/205.24
[58] Field of Search ............ 128/200.24, 202.27, 128/204.28, 205.13, 205.17, 205.24, 202.28, 202.29, 203.11, 203.28, 204.18

[56] References Cited

U.S. PATENT DOCUMENTS

| | | | |
|---|---|---|---|
| 4,071,025 | 1/1978 | Kohnke | 128/205.13 |
| 5,025,829 | 6/1991 | Edwards et al. | 137/512 |
| 5,427,091 | 6/1995 | Phillips | 128/205.15 |
| 5,456,249 | 10/1995 | Kirk | 128/205.13 |

FOREIGN PATENT DOCUMENTS

| | | |
|---|---|---|
| 0 367 285 A3 | 5/1990 | European Pat. Off. . |
| 0 474 069 A1 | 3/1992 | European Pat. Off. . |
| A 2271845 | 12/1975 | France . |
| 24 24 798 B2 | 3/1976 | Germany . |
| 31 35 276 A1 | 6/1982 | Germany . |
| 42 34 668 A1 | 4/1993 | Germany . |

OTHER PUBLICATIONS

V.O. Lang, H.R.P. System 2000—A New Universally Applicable Ventilation System For Single Or Limited Mulitple Use With High Bacteriologic–Hygienical Safety, *Anaesthesist* 28:474–483 Springer–Verlag, 1979.

*Primary Examiner*—Vincent Millin
*Assistant Examiner*—Eric P. Raciti
*Attorney, Agent, or Firm*—Panitch Schwarze Jacobs & Nadel, P.C.

[57] ABSTRACT

A respiratory gas container has a flexible bag having an opening with a valve housing arranged in the opening area housing having an upper part and a lower part as well as at least one gas discharge and one gas inlet valve and a connection piece. In order to be able to decontaminate the respiratory gas container reliably and to be able to recognize and eliminate functional disturbances easily, the lower part is mounted substantially within the bag, whereby the lower part has at least one gas discharge valve within the opening. The upper part is mounted substantially outside the bag, whereby it has at least one gas inlet valve and a connection opening as well a fixing element with gas outlet openings mounted in the area of the bag opening. The lower part is detachably joined with the upper part, whereby at lease one connection opening is connected with a gas inlet opening of the lower part through a hollow space of the upper part.

13 Claims, 2 Drawing Sheets

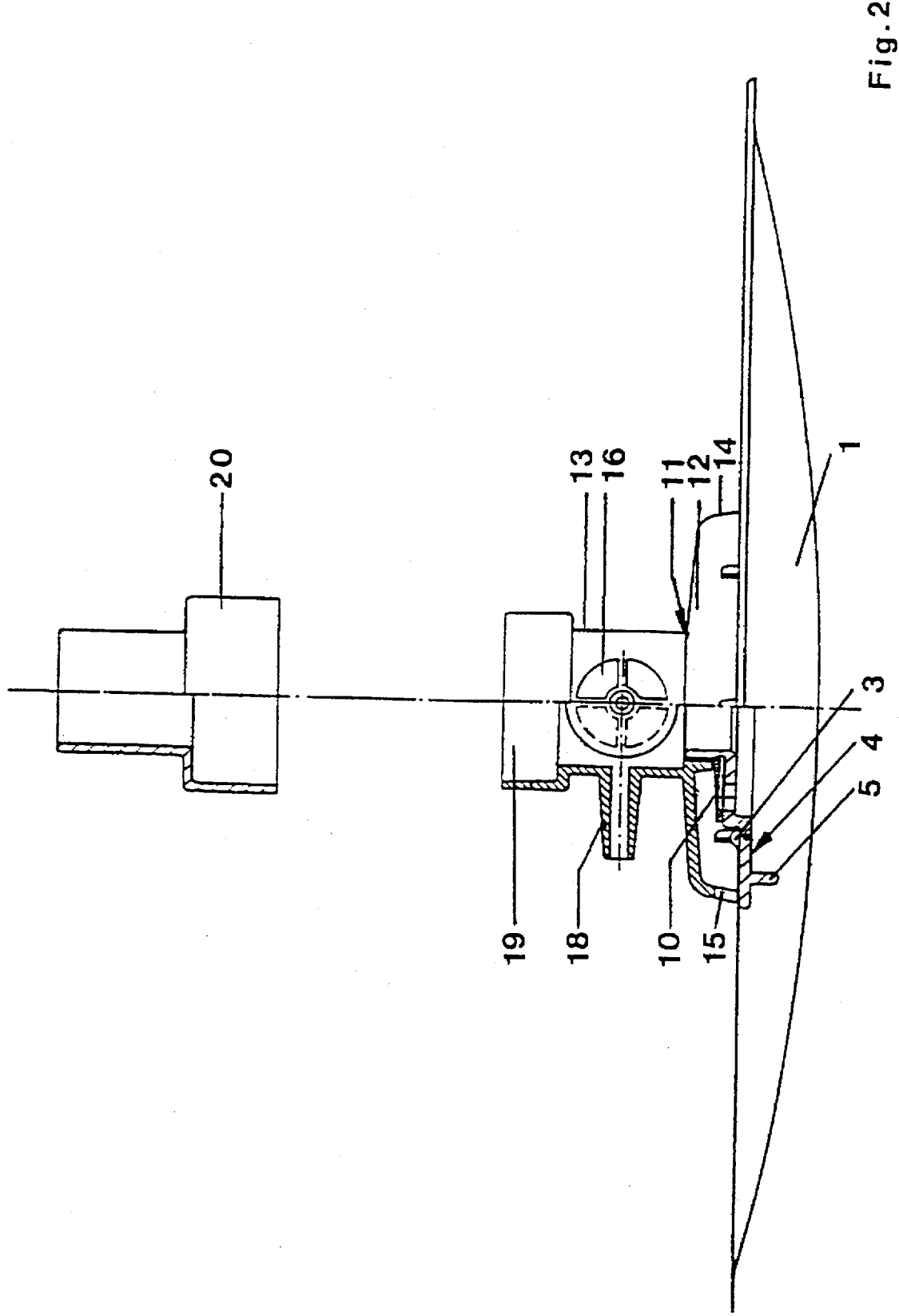

RESPIRATORY GAS CONTAINER

FIELD OF THE INVENTION

The invention concerns a respiratory gas container with a flexible bag with an opening having a valve housing installed in the area of the opening, the valve housing having an upper part and a lower part as well as at least one gas inlet and gas discharge valve and a connection piece.

BACKGROUND OF THE INVENTION

Such a respiratory gas container is known from the "Maintenance Table for AMBU® Respirator Bags." Here the respiratory gas container is described as an oxygen reservoir. This respiratory gas container has a flexible bag at whose opening a valve housing is inseparably installed, whereby a lower part of the valve housing is pressed into an upper part of the valve housing from inside the bag. A connection piece is mounted on the upper part. The valve housing has valves for gas inlet (admission) and gas outlet (discharge), which are installed between the upper and lower parts.

There exists the possibility of a contamination with pathogens in connection with use of the respiratory gas container on patients, so that the respiratory gas container must be cleaned thoroughly on a regular basis. This can, however, be only incompletely implemented with reasonable expenditure with the known embodiment, since the bag and the valve housing are not accessible from inside, just as the valves. A possible functional disturbance of the respiratory gas container can neither be concretely determined nor eliminated, as the individual parts are not accessible by themselves. Hence, it is not only due to faulty cleansing possibilities (the respiratory gas container cannot, for example, be autoclaved), but also due to the back of possibility of remedying functional disturbances, that it is frequently necessary to exchange respiratory gas containers for new ones.

SUMMARY OF THE INVENTION

Proceeding from the state of the art as described, an object of the present invention is to produce a respiratory gas container of the above-described type which can be decontaminated reliably and with which functional disturbances can easily be recognized and eliminated.

This object is solved for a respiratory gas container with a flexible bag having an opening with a valve housing mounted in the area of the opening, the housing having an upper part, a lower part, at least one gas inlet and gas discharge valve, and a connection piece, such that the lower part is substantially mounted within the bag, whereby the lower part has at least one gas discharge valve within the opening, that the upper part is mounted substantially outside the bag and has at least one gas inlet valve and a connection opening as well as a fixing element with gas outlet openings arranged in the area of the bag opening, and that the lower part is detachably connected with the upper part, whereby at least one connection opening is joined with a gas inlet opening of the lower part through a hollow space in the upper part. The lower part and the fixing element of the upper part can have a dish-like configuration, i.e., their radial extension is greater than the axial extension in relation to an axis perpendicular to the opening.

A respiratory gas container of this type can be constructed almost without inaccessible parts in which germs can become established and resist cleaning. The respiratory gas container may be wholly disassembled, and can thus be easily cleaned (even in individual parts). Functional disturbances may also be eliminated through the possibility of disassembly without having to replace the complete respiratory gas container. The individual valves are easily accessible and consequently can also be easily checked.

It is expedient for a simple construction that the gas discharge valve of the lower part be formed by gas discharge openings and a membrane, which are arranged around the gas inlet opening of the lower part. In this way the function of the valve may be easily examined, and if necessary, a new membrane may be installed without great effort even by lay persons.

It is appropriate that the opening of the bag be constructed in circular form, since such a construction is first of all easily realized in finishing technique and secondly guarantees a high functional safety of the respiratory gas container through uniform construction in all directions. The connection between upper part and lower part takes place advantageously by the gas inlet opening of the lower part and the upper part being connected with each other by threads. It is suitable for a simple separation of the two parts from each other that the side of the lower part facing away from the upper part has grip elements so that the lower part mounted in the bag can be better handled.

It is further expedient that the dish-like fixing element have a rim bent toward the bag, the edge of the rim lying against the bag when the housing is assembled, and especially that the gas outlet openings of the upper part be arranged on the bent rim. It is advantageous for an exact fixation of the valve housing on the bag that the lower part have an elevation within the opening, with the elevation lying on the edge of the opening, whereby the edge of the opening is constructed as a rim band. The height of the rim band can especially roughly correspond to the height of the elevation.

It is furthermore advantageous that at least one gas inlet valve be arranged on the connection piece in order to guarantee simple gas conduction as well as a high functional reliability.

The connection piece can have two connection openings with different diameters in an advantageous embodiment of the invention whereby, for example, oxygen can be introduced through the one connection opening, while the second connection opening can be attached to a respirator bag or (if necessary via a patient valve) be directly connected with a breathing mask. In this way the respiratory gas container can be used for various purposes (for example for enrichment of the oxygen of the air administered to the patient through the respirator bag, for oxygen therapy, or for rebreathing therapy in connection with a hyperventilation syndrome).

It is advantageous for the maintenance of the respiratory gas container that the bag be constructed of a gas-tight, autoclavable material and/or that the valve housing be made substantially of a transparent material, whereby the latter also serves for rapid recognition of operating disturbances.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings:

FIG. 2 is a schematic representation of the respiratory gas container, partially in section.

DETAILED DESCRIPTION OF PREFERRED EMBODIMENTS

Figure 1:
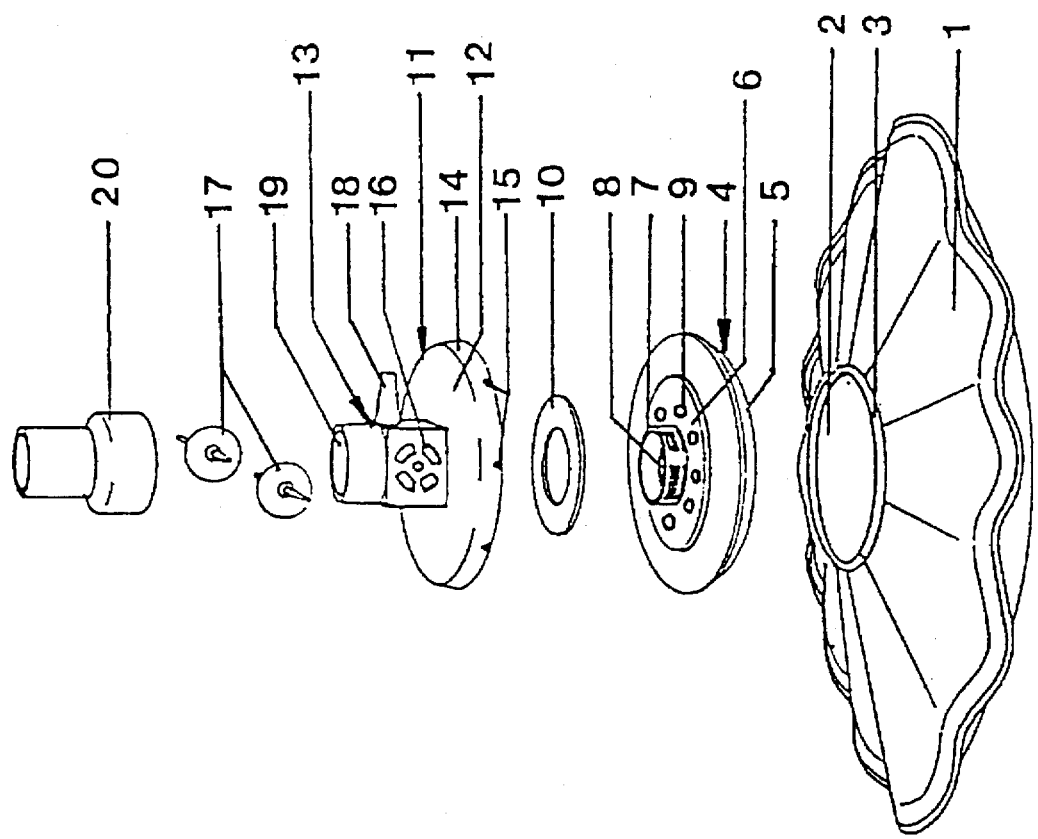
FIG. 1 is an exploded representation of a respiratory gas container according to the invention.

The respiratory gas container has a flexible bag 1 of siliconized polyamide which basically comprises two circular parts connected with each other on their outer periphery, wherein the one part has a circular opening 2 in its center. The opening is surrounded by a rim band made of the bag material.

The lower part 4 of the valve housing is mounted in the bag 1. On its underside, which is directed toward the bag interior, the lower part 4 has grip elements 5 which serve to improve handling of the lower part 4 in assembling and disassembling. The lower part is basically constructed from a flat, circular disk of a transparent plastic (e.g. polysulfone). In the center of this disk is arranged a circular elevation 6 whose diameter corresponds to that of the opening 2 and whose height corresponds to the height of the rim band, so that this elevation 6 closes the opening 2 of the bag 1.

In the center of the elevation 6 is mounted a threaded pipe 7 which surrounds the gas inlet opening 8 of the lower part 4. The gas discharge openings 9 are arranged circularly around the gas inlet opening 8 on the elevation, upon which a ring-shaped silicon rubber membrane 10 lies. The gas discharge openings 9 arranged upon the elevation 6 and the ring-shaped membrane 10 thereby form the gas discharge valve of the lower part 4. The essentially flat surface of the lower part arranged around the elevation 6 lies lightly on the inside of the bag.

The upper part 11 of the valve housing is screwed onto the lower part 4. The upper part 11 basically comprises a fixing element 12 and a connection piece 13. The fixing element presents a dish-like, flat, circular surface in the example depicted, the outer rim 14 of which is bent toward the bag 1 and which lies loosely on this. Gas outlet openings 15 are arranged on the outer edge of the rim 14 through which gas can escape which exits the bag 1 through the gas discharge valve of the lower part 4. The rim 14 lies in the region of the lower part 4 on the bag 1, i.e., the fixing element 12 with its rim 14 has a diameter which is not greater than the diameter of the lower part 4. It is also conceivable to make the fixing element 12 with a larger diameter, but then the function of the respiratory gas container is no longer assured owing to possible defective anchoring of the bag 1 on the valve housing.

The connection piece 13 has four flat side surfaces arranged on the fixing element. Gas inlet valves 16 are arranged on two opposed flat side surfaces, in connection with which the valve openings are covered by circular silicon rubber valve membranes 17 in the interior of the connection piece 13. A connection opening 18 is arranged on a third flat side surface, which is suitable for hooking up an oxygen source. A connection opening 19 is arranged centrally to the upper part 11 on the connection piece 13, which is suitable for connection to a conventional respirator bag.

Normally both connection openings 18, 19 have different diameters in order to avoid confusion during the use of the respiratory gas container. The connection opening 19 for connection to a respirator bag thereby has a substantially greater diameter than the connection opening 18.

An adapter 20 may be attached on the connection opening 19, by means of which the respiratory gas container may be connected with a respirator mask, directly or through interposition of a known patient valve. A connection of this type serves, in the event of interposition of a patient valve, for direct provision of the patient with oxygen, i.e. for oxygen therapy, while a connection of the respiratory gas container directly to a respirator mask serves for rebreathing therapy in the event of a hyperventilation syndrome. The respiratory gas container has a maximum volume of approximately 1200 ml in the embodiment described.

Owing to the fact that the upper part 11 of the valve housing is formed substantially of a transparent plastic, coarse impurities or functional disturbances in the respiratory gas bag may also be rapidly recognized and easily eliminated owing to its simple ability for disassembly. Possibly defective parts are easily exchangeable, and the parts of the respiratory gas container can be reliably cleaned, as there are no inaccessible places in which impurities can accumulate.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

I claim:

1. A respiratory gas container comprising a flexible bag (1) having an opening (2) and a valve housing mounted in a vicinity of the opening, the valve housing comprising an upper part (11), a lower part (4), at least one gas inlet and gas discharge valve, and a connection piece (13), the lower part (4) being mounted substantially within the bag (1) and having a gas inlet opening (8) and at least one gas discharge valve within the bag opening (2), the upper part (11) being mounted substantially outside the bag (1) and having at least one gas inlet valve (16), at least one connection opening (18, 19), and a fixing element (12) having gas outlet openings (15) arranged in a vicinity of the bag opening (2), the lower part (4) being separably connected with the upper part (11), and at least one connection opening (18, 19) being joined with the gas inlet opening (8) of the lower part through a hollow space of the upper part (11).

2. The respiratory gas container according to claim 1, wherein the at least one gas discharge valve of the lower part comprises gas discharge openings (9) and a membrane (10) arranged around the gas inlet opening (8).

3. The respiratory gas container according to claim 1, wherein the bag opening (2) has a circular configuration.

4. The respiratory gas container according to claim 1, wherein the gas inlet opening (8) and the upper part (11) are joined with each other by threads.

5. The respiratory gas container according to claim 1, wherein a side of the lower part (4) facing away from the upper part (11) has grip elements (5).

6. The respiratory gas container according to claim 1, wherein the bag (1) comprises a gas-tight, autoclavable material.

7. The respiratory gas container according to claim 1, wherein the valve housing comprises substantially a transparent material.

8. The respiratory gas container according to claim 1, wherein the lower part (4) has an elevation (6) within the bag opening (2), the elevation lying against an edge of the bag opening (2), and the edge of the bag opening (2) being in the form of a rim band (3).

9. The respiratory gas container according to claim 8, wherein the rim band (3) has a height roughly corresponding to the height of the elevation (6).

10. The respiratory gas container according to claim 1, wherein at least one gas inlet valve (16) is arranged on the connection piece (13).

11. The respiratory gas container according to claim 10, wherein the connection piece (13) has two connection openings (18, 19) having different diameters.

12. The respiratory gas container according to claim 1, wherein fixing element (12) is dish-shaped and has a rim (14) bent toward the bag (1), an edge of the rim lying on the bag (1) when the parts are assembled.

13. The respiratory gas container according to claim 12, wherein the gas outlet openings (15) of the upper part (11) are arranged on the bent rim (14).

* * * * *